(12) United States Patent
Pressacco et al.

(10) Patent No.: US 12,150,658 B2
(45) Date of Patent: Nov. 26, 2024

(54) GLENOID POSITIONING DEVICE

(71) Applicant: LIMACORPORATE S.P.A., San Daniele del Friuli (IT)

(72) Inventors: Michele Pressacco, Martignacco (IT); Marco Dosso, Lumignacco (IT); Francesco Della Vedova, Cassacco (IT)

(73) Assignee: Limacorporate S.p.A., San Daniele del Friuli (IT)

( * ) Notice: Subject to any disclaimer, the term of this patent is extended or adjusted under 35 U.S.C. 154(b) by 90 days.

(21) Appl. No.: 17/785,752

(22) PCT Filed: Dec. 10, 2020

(86) PCT No.: PCT/EP2020/085554
§ 371 (c)(1),
(2) Date: Jun. 15, 2022

(87) PCT Pub. No.: WO2021/122317
PCT Pub. Date: Jun. 24, 2021

(65) Prior Publication Data
US 2023/0064917 A1 Mar. 2, 2023

(30) Foreign Application Priority Data
Dec. 16, 2019 (IT) .................... 102019000024069

(51) Int. Cl.
*A61F 2/40* (2006.01)
*A61B 17/15* (2006.01)
(Continued)

(52) U.S. Cl.
CPC ........ *A61B 17/1778* (2016.11); *A61B 17/848* (2013.01); *A61B 17/90* (2021.08); *A61F 2/4081* (2013.01)

(58) Field of Classification Search
None
See application file for complete search history.

(56) References Cited

U.S. PATENT DOCUMENTS

| | | | | |
|---|---|---|---|---|
| 2,148,692 A | * | 2/1939 | Guinn | A61C 11/084 433/65 |
| 5,540,697 A | * | 7/1996 | Rehmann | A61F 2/4609 606/100 |

(Continued)

FOREIGN PATENT DOCUMENTS

| | | | | |
|---|---|---|---|---|
| CN | 102946814 A | * | 2/2013 | ......... A61B 17/1684 |
| FR | 3104403 A1 | * | 6/2021 | ......... A61B 17/1778 |

(Continued)

OTHER PUBLICATIONS

International Search Report dated Feb. 25, 2021 issued in connection with PCT/EP2020/085554.

(Continued)

*Primary Examiner* — Ann Schillinger
(74) *Attorney, Agent, or Firm* — Akerman LLP

(57) ABSTRACT

A glenoid positioning device (100), in particular for a Kirschner wire, comprising: a hub (101) with a reference through-hole (110) and comprising three housings (102a, 102b, 102c) arranged radially; three slide elements (103a, 103b, 103c) slidably housed within the three housings (102a, 102b, 102c), respectively, and configured to interact with a glenoid cavity; wherein the three slide elements (103a, 103b, 103c) are configured to be radially extended or retracted to identify a circular area (2) of a glenoid cavity.

13 Claims, 5 Drawing Sheets

(51) Int. Cl.
*A61B 17/16* (2006.01)
*A61B 17/17* (2006.01)
*A61B 17/84* (2006.01)
*A61B 17/90* (2006.01)

(56) References Cited

U.S. PATENT DOCUMENTS

| | | | | |
|---|---|---|---|---|
| 6,884,246 | B1* | 4/2005 | Sonnabend | A61B 17/142 606/82 |
| 7,879,042 | B2* | 2/2011 | Long | A61F 2/4609 623/22.12 |
| 9,402,650 | B2* | 8/2016 | Boileau | A61B 17/56 |
| 10,363,047 | B2* | 7/2019 | Kehres | A61B 17/1659 |
| 10,405,993 | B2* | 9/2019 | Deransart | A61B 17/1739 |
| 10,631,880 | B1* | 4/2020 | Callahan | A61B 17/17 |
| 10,952,872 | B2* | 3/2021 | Pressacco | A61B 17/1617 |
| 11,026,810 | B2* | 6/2021 | Davenport | A61F 2/4609 |
| 11,123,086 | B1* | 9/2021 | Callahan | A61B 17/1615 |
| 2006/0100638 | A1* | 5/2006 | Sarin | A61B 90/36 606/102 |
| 2006/0195105 | A1* | 8/2006 | Teeny | A61F 2/4609 606/76 |
| 2009/0234453 | A1* | 9/2009 | Steinberg | A61B 17/1617 606/1 |
| 2009/0254091 | A1* | 10/2009 | Long | A61B 17/1684 606/87 |
| 2012/0143267 | A1* | 6/2012 | Iannotti | A61B 17/1746 606/86 R |
| 2012/0239051 | A1 | 9/2012 | De Wilde et al. | |
| 2013/0261629 | A1* | 10/2013 | Anthony | A61B 17/32053 606/80 |
| 2015/0250614 | A1* | 9/2015 | Davenport | A61F 2/4609 606/99 |
| 2016/0296285 | A1 | 10/2016 | Chaoui et al. | |
| 2016/0342766 | A1* | 11/2016 | Darwood | A61B 17/17 |
| 2019/0015116 | A1 | 1/2019 | Gargac et al. | |
| 2019/0015221 | A1* | 1/2019 | Neichel | A61F 2/4081 |
| 2019/0343658 | A1 | 11/2019 | Deransart et al. | |
| 2021/0045895 | A1* | 2/2021 | Sapio | A61F 2/4003 |
| 2021/0259844 | A1* | 8/2021 | Penninger | A61F 2/4612 |

FOREIGN PATENT DOCUMENTS

| | | | | |
|---|---|---|---|---|
| WO | WO-2010017307 | A1 * | 2/2010 | A61B 17/025 |
| WO | WO-2017029173 | A1 * | 2/2017 | A61F 2/4014 |
| WO | WO-2020033911 | A1 * | 2/2020 | A61B 17/1778 |

OTHER PUBLICATIONS

Written Opinion of the International Searching Authority dated Feb. 25, 2021 issued in connection with PCT/EP2020/085554.
International Search Report dated Feb. 15, 2021 issued in connection with PCT/EP2020/085554.
Written Opinion of the International Searching Authority dated Feb. 15, 2021 issued in connection with PCT/EP2020/085554.

* cited by examiner

GLENOID POSITIONING DEVICE

CROSS-REFERENCE TO RELATED APPLICATIONS

This application is a national phase of PCT/EP2020/085554, filed Dec. 10, 2020, and claims priority to Italian Patent Application No. 102019000024069, filed Dec. 16, 2019, the entire contents of both of which are hereby incorporated by reference.

FIELD OF APPLICATION

The present invention relates to a glenoid positioning device, in particular for positioning a reference into the glenoid cavity during a shoulder prosthesis implantation surgery.

The invention finds particular utility in implantation surgery of a shoulder prosthesis, both anatomical and reverse; the following description is made with reference to this specific application field as exemplificatory disclosure.

In general, the invention may be used to find a central positioning within a glenoid cavity of a scapula and to fix a reference there, such as for instance a Kirschner wire, which is usable for further operations during implantation of a shoulder prosthesis.

PRIOR ART

In the shoulder prosthesis field, the use of prostheses is now widespread, typically modular prostheses constituted by a plurality of elements that can be combined with each other to obtain an anatomical or reverse prosthesis, and possibly to convert the prosthesis from anatomic to reverse.

Some commonly used prostheses involve the use of a glenoid anchor inserted in a hole previously obtained substantially in the center of the glenoid cavity. In the event of an anatomical prosthesis, a polyethylene insert is typically fixed on the glenoid anchor, whereas in the event of a reverse prosthesis, a convex glenoid joint component, called glenosphere, is typically fixed on the glenoid anchor.

A difficulty that arises is to accurately fix, in a central position in the glenoid cavity, the appropriate anchor so as to have the center of the prosthesis component coupled thereto aligned with the center of the glenoid cavity.

In the prior art, there are in fact reproducibility problems of the optimal positioning in the center of the glenoid cavity, which can compromise the effectiveness of a shoulder prosthesis.

An object of the present invention is to provide a glenoid positioning device having structural and functional characteristics such as to overcome the drawbacks complained of with reference to the prior art.

A further object of the present invention is to allow the correct positioning of a reference, such as for example a Kirschner wire, which acts as a guide for an implantation of a glenoid part of a shoulder prosthesis, be it anatomical or reverse.

A further object of the present invention is also to allow the correct positioning of a reference in the center of the glenoid fossa of scapula, for a better positioning of a shoulder prosthesis.

SUMMARY OF THE INVENTION

The solution idea underlying the present invention is to make a mechanical guide that allows the approximation of a glenoid cavity by means of three circumferential points, meanwhile allowing the positioning of a reference in the center of the circumference thus identified, in particular for fixing a reference.

Advantageously, the present invention allows a more reliable identification of the center of the glenoid cavity, allowing a more accurate and repeatable positioning of a reference, constituted for instance by a Kirschner wire, used during a shoulder prosthesis implantation.

Based on this solution idea, there is provided a glenoid positioning device comprising: a hub with a reference through-hole and comprising three radially arranged housings; three slide elements slidably housed within said three housings, respectively, and configured to interact with a glenoid cavity; the three slide elements are configured to be radially extended or retracted to identify a circular area of a glenoid cavity.

The slide elements are extended or retracted synchronously with each other. In this way, they may advantageously pass, when radially extended, a glenoid margin in a sagittal plane in the fore/aft direction, and thus provide a centering reference having a variable radius in a circumference thus identified, in particular for fixing a reference, for example for fixing a Kirschner wire.

Preferably, the glenoid positioning device further comprises a central spindle axially associated with the hub and rotatable therein; and three connection bars connecting each slide element with the central spindle. The three slide elements are thus configured to be radially extended or retracted by the action of the three connection bars operated by a rotation of said central spindle.

In this way, the three slide elements allow identifying a circular area of a glenoid cavity, and the central spindle is configured to identify a center of the circular area for positioning a reference in a center of a glenoid fossa of scapula. Thus, advantageously, it becomes possible to position a reference in the center of the fossa of scapula of a glenoid cavity in an accurate and repeatable manner.

Preferably, two slide elements are substantially opposite each other and have protruding ends to externally grasp a glenoid portion of a scapula; preferably a third slide element that is transversal to the first two provides a visual reference to verify the alignment with an own circumference of the glenoid cavity.

Preferably, the hub and the central spindle comprise respective through-holes that are axially aligned and configured for the axial insertion of a reference, for instance a Kirschner wire.

Advantageously, the hub and the central spindle also comprise respective side access slots that are alignable to each other to allow a side extraction of the reference, for instance a Kirschner wire, i.e. a removal of the glenoid positioning device from the reference positioned in the glenoid area, once the reference has been correctly implanted. Advantageously, this allows decoupling the glenoid positioning device from the reference.

Further characteristics and advantages of the invention will become clearer from the following detailed description, provided for illustrative and non-limiting purposes, and from the claims that are an integral part of the present description.

In different figures, analogous elements will be indicated by analogous reference numbers.

DETAILED DESCRIPTION

Figure 1:
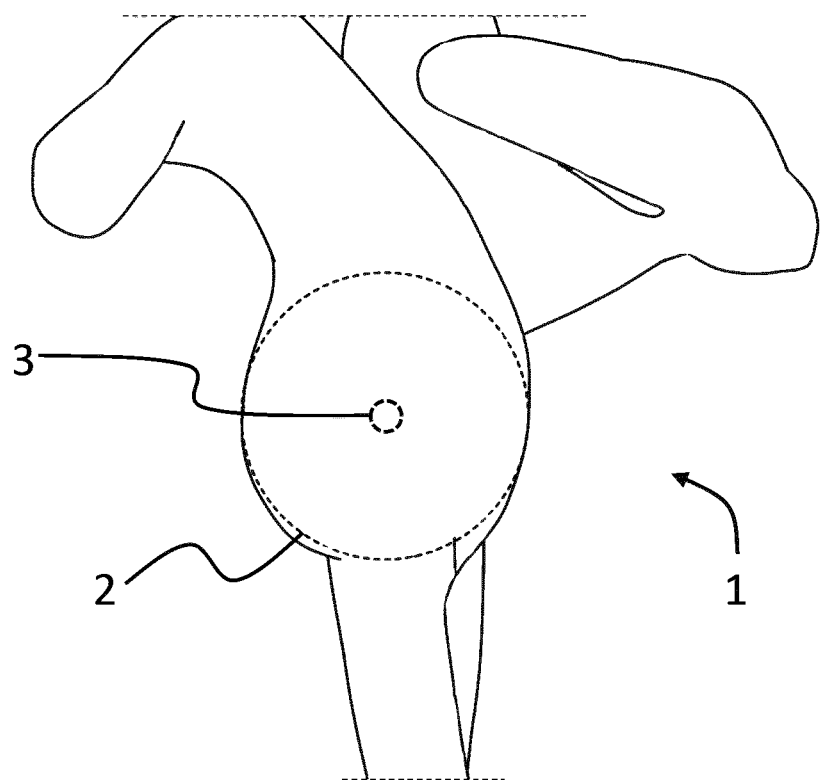
FIG. 1 shows a side schematic view of a scapula, in which a glenoid cavity is visible.

FIG. 1 shows a side schematic view of a scapula 1. Analysing the shape of the glenoid cavity of the scapula 1, it is possible to identify a circular area 2 in the lower part thereof, defined as glenoid "fossa" of the scapula and represented by the circumference 2.

As it will be clear hereinafter, a glenoid positioning device according to the present invention allows precisely determining a centre 3 of the glenoid cavity 2, in particular in order to position a reference, for instance a Kirschner wire, which will be useful as a guide for the implantation of a glenoid part of a shoulder prosthesis, of the anatomic or of the reverse type.

Usable references for implantation in the glenoid cavity 2, in cooperation with the glenoid positioning device of the present invention include, not limited to: Kirschner wires ("K-wires") or "Steinmann pins" or other types of "pins".

Figure 2:
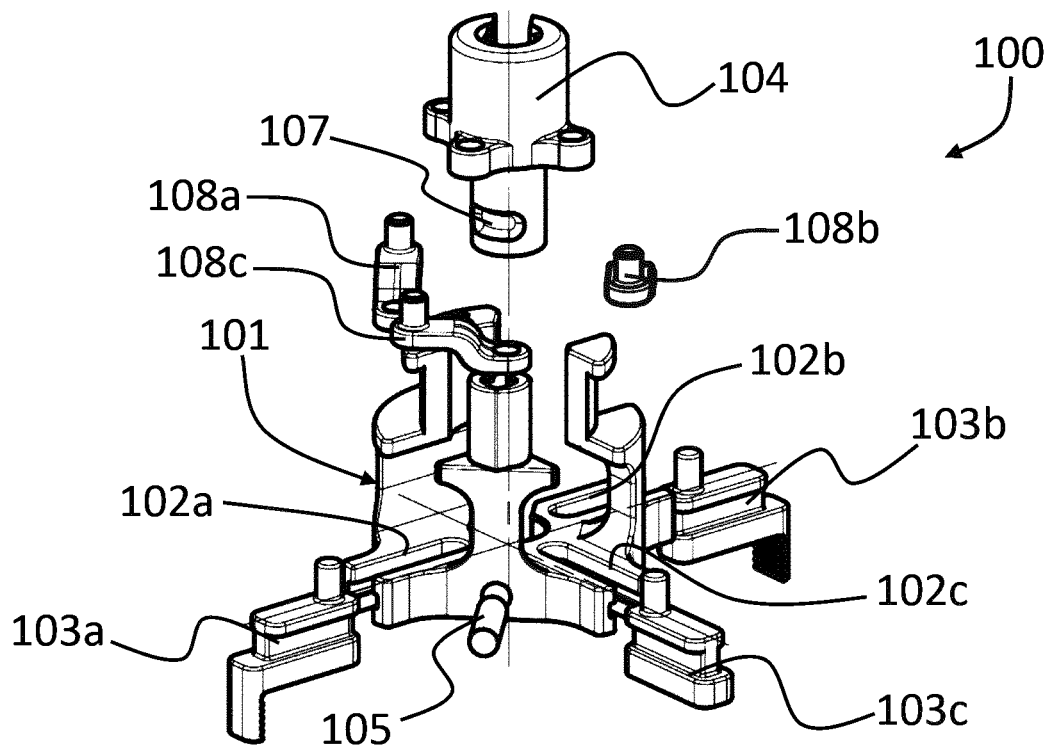
FIG. 2 shows an exploded perspective view of an embodiment of a glenoid positioning device according to the present invention.

FIG. 2 shows a perspective view of an embodiment of a glenoid positioning device 100 according to the present invention. The representation of the glenoid positioning device 100 is presented as an "exploded" view, so as to more effectively display the elements, even the internal ones, of the glenoid positioning device 100. The glenoid positioning device 100 will be further represented and described even in an assembled form thereof.

The glenoid positioning device 100 comprises a hub 101, with a reference through-hole 110 that will be described hereinafter, and comprising three housings 102a, 102b, and 102c radially arranged in the hub 101.

The glenoid positioning device 100 then comprises three slide elements 103a, 103b and 103c, slidably housed within the three housings 102a, 102b, and 102c, respectively.

As it will become clearer hereinafter, the three slide elements 103a, 103b and 103c are configured to interact with a glenoid cavity, during the use of the glenoid positioning device 100.

The glenoid positioning device 100 further comprises a central spindle 104 axially associated with the hub 101 and rotatable therein. Preferably, the hub 101 further comprises a pin 105 configured to engage into a radial groove 107 of the hub 104, so as to allow a rotation of the central spindle 104 within the hub 101, but preventing a translation of the central spindle 104 in an axial direction.

The glenoid positioning device 100 further comprises three connection bars 108a, 108b and 108c connecting each of the three slide elements 103a, 103b and 103c, respectively, with respective seats formed in the central spindle 104.

In the glenoid positioning device 100, the three slide elements 103a, 103b and 103c are thus configured to be radially extended or retracted, to identify a circular area of the glenoid cavity.

In particular, the three slide elements 103a, 103b and 103c are thus configured to be radially extended or retracted by the action of the three connection bars 108a, 108b and 108c moved by a rotation of the central spindle 104.

The rotation of the central spindle 104 is preferably performed, during the use, by means of a knob associable with the glenoid positioning device 100, not represented in the figures.

Figure 3:
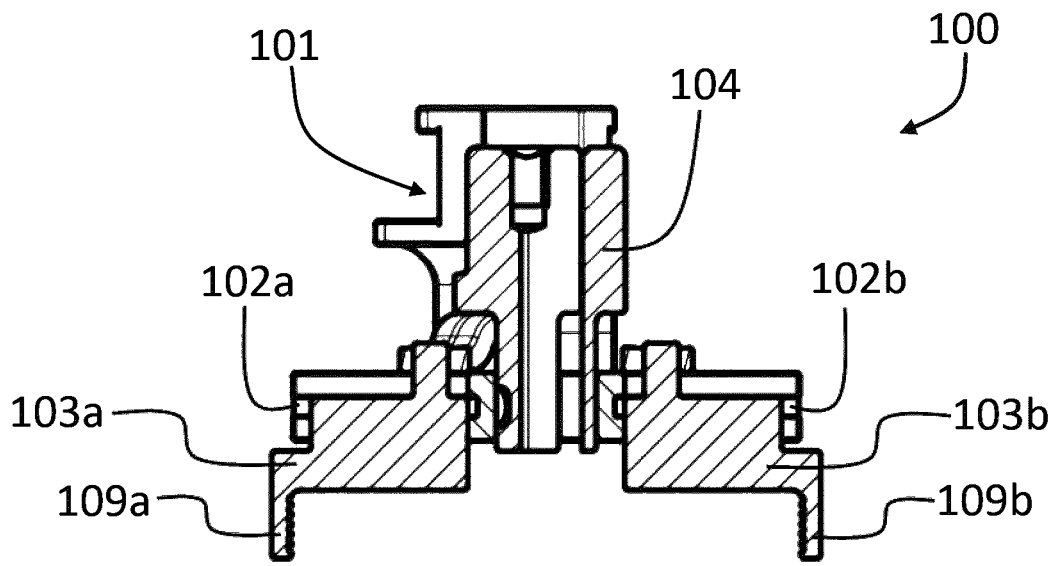
FIG. 3 shows a sectional side view of an embodiment of a glenoid positioning device according to the present invention, in the assembled form.

FIG. 3 shows a sectional side view of the glenoid positioning device 100, in the assembled form.

In this side view it is possible to observe that a first slide element 103a and a second slide element 103b comprise respective protruding ends 109a and 109b configured to externally grasp a glenoid portion of a scapula. In particular, the protruding ends 109a and 109b comprise internal machined or knurled internal surfaces, configured to increase friction with a bone surface during the use of the glenoid positioning device 100, in the manner that will be described in the following.

Figure 4:
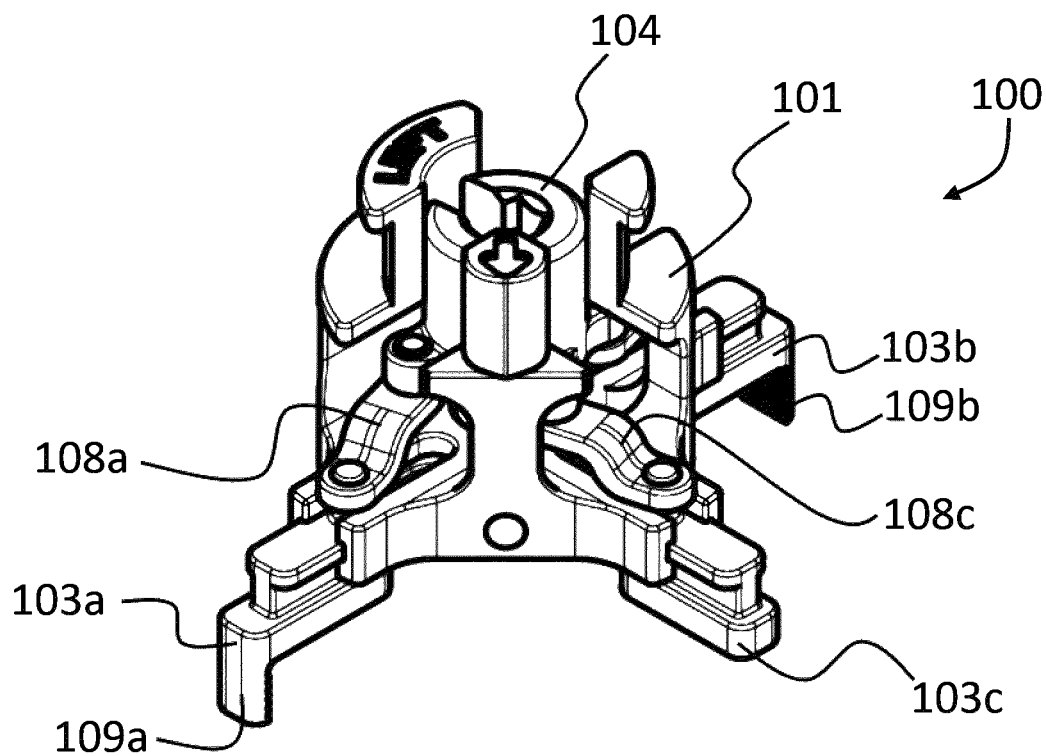
FIG. 4 shows a perspective view of an embodiment of a glenoid positioning device according to the present invention, in an open configuration.

FIG. 4 shows a perspective view of the glenoid positioning device 100, in an open configuration.

As visible in this figure, the first slide element 103a and the second slide element 103b are substantially opposite each other, i.e. aligned on opposite sides with respect to the hub 101 and to the central spindle 104.

The third slide element 103c is substantially aligned in the transversal direction with respect to the first two slide elements 103a and 103b. As it will be described in the following, the third slide element 103c is in particular configured to provide a visual reference by means of an own end: indeed for the scapular anatomy, it is not possible to provide for the third slide element 103c a protruding end similar to the protruding ends 109a and 109b.

In this view it is possible to view that the three connection bars 108a, 108b and 108c are connected to the central spindle 104 and to the three slide elements 103a, 103b and 103c, respectively, by means of pins, so as to form a triple system of the rod-crank type.

Figure 6:
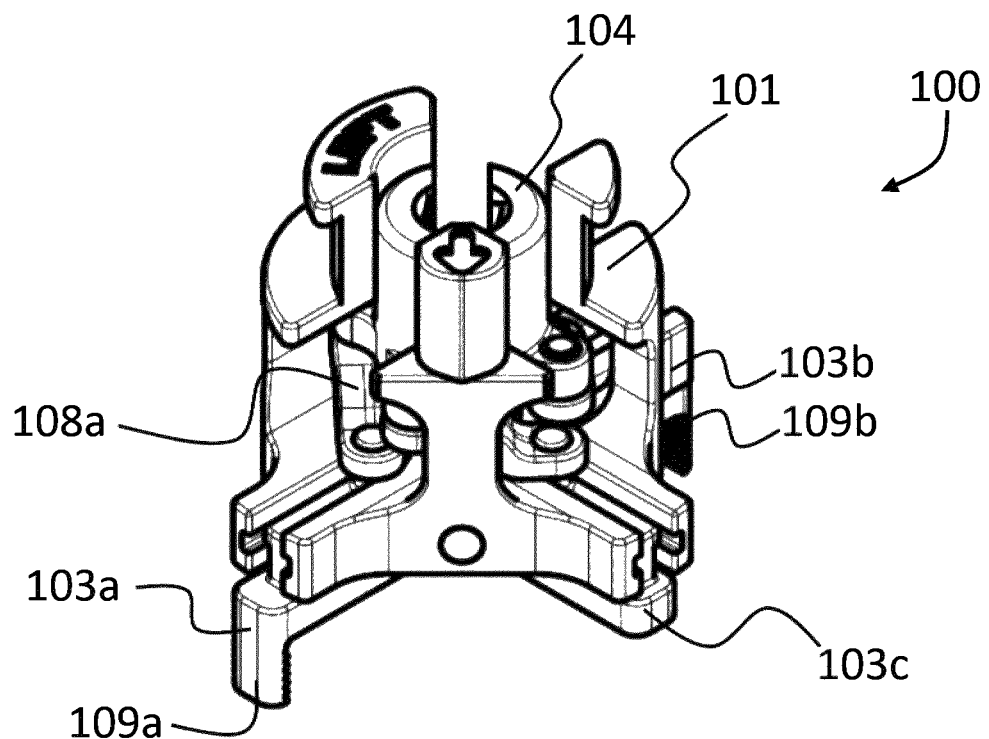
FIG. 6 shows a perspective view of an embodiment of a glenoid positioning device of the present invention, in a closed configuration.

In particular, the triple system of the rod-crank type of the glenoid positioning device 100 is configured, during the rotation of the central spindle 104, to extend in a first phase the three slide elements 103a, 103b and 103 from a maximum closure position, represented in the subsequent FIG. 6, up to a maximum opening position represented in FIG. 4 herein discussed.

Furthermore, during a rotation of the central spindle 104 in the opposite direction, the three slide elements 103a, 103b and 103c are retracted in a further position, at least partially retracted, in which in use they interact with a scapular bone, as it will be described hereinafter.

Figure 5:
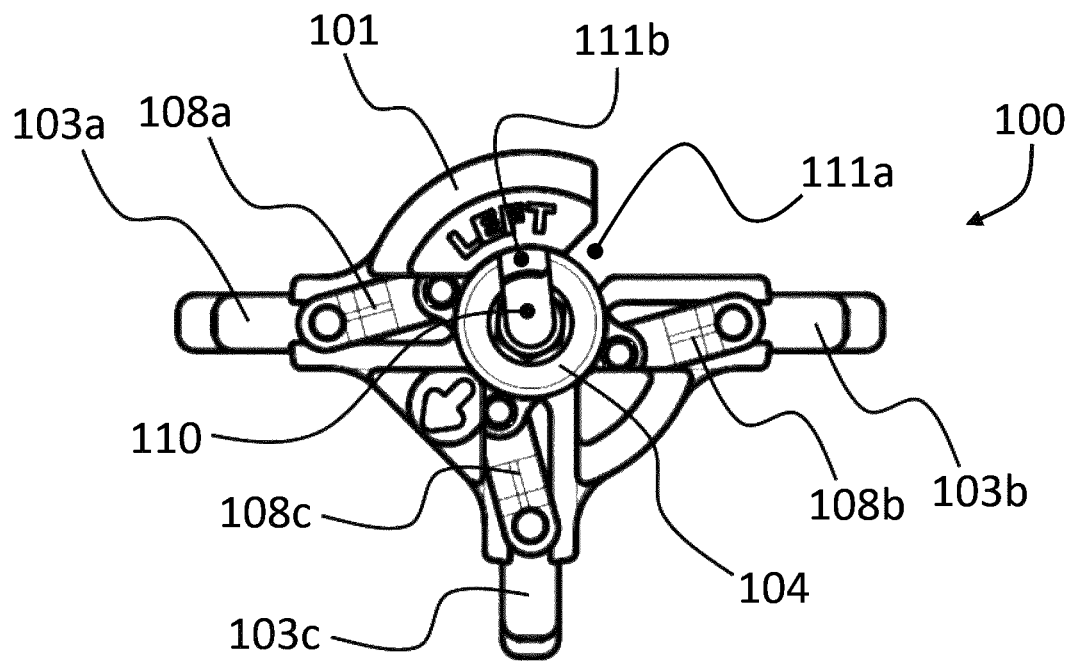
FIG. 5 shows an upper view of the glenoid positioning device of FIG. 4.

FIG. 5 shows an upper view of the glenoid positioning device 100.

In this view it is possible to observe that the hub 101 and the central spindle 104 comprise respective reference through-holes 110 axially aligned to each other, which are configured for the axial insertion of a reference, for instance of a Kirschner wire.

FIG. 6 shows a perspective view of the glenoid positioning device 100, in a closed configuration.

Comparing the view of FIG. 6 with the view of FIG. 4, it is possible to observe that in the glenoid positioning device 100 the slide elements 103a, 103b and 103c are configured to be extended or retracted.

Figure 7:
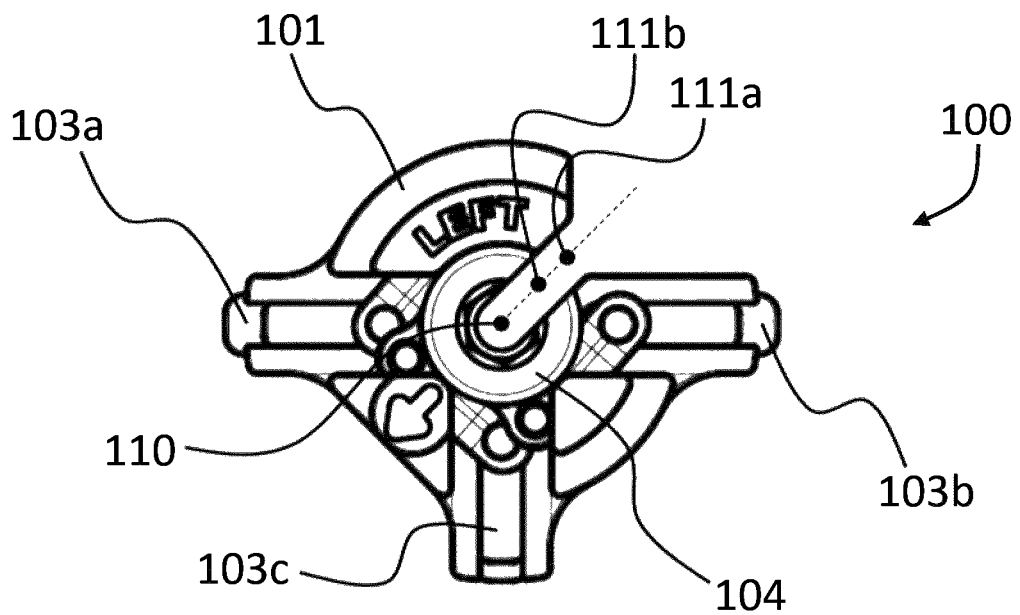
FIG. 7 shows an upper view of the glenoid positioning device of FIG. 6.

FIG. 7 shows an upper view of the glenoid positioning device 100.

Still comparing the view of FIG. 5 with the view of FIG. 7, it is possible to observe that in the glenoid positioning device 100 the slide elements 103a, 103b and 103c are configured to be extended or retracted, with the respective ends lying on a same circumference, which has a radius that is variable with the rotation of the central spindle 104.

Furthermore, it is possible to view that the hub 101 and the central spindle 104 comprise respective side access slots 111a and 111b to respective reference through-holes 110.

Said side access slots 111a and 111b are aligned to each other, in particular for an angular position deriving from the rotation of the central spindle 104.

Said angular position is preferably a complete closure position of the glenoid positioning device 100 as represented in FIG. 7, so as to allow a side extraction of a reference such as for instance a Kirschner wire, inserted in the axial reference through-hole 110.

In this way, it is possible to easily remove the glenoid positioning device 100 by means of a side movement, once the reference has been positioned and implanted in the center of the glenoid fossa of scapula.

Figure 8:
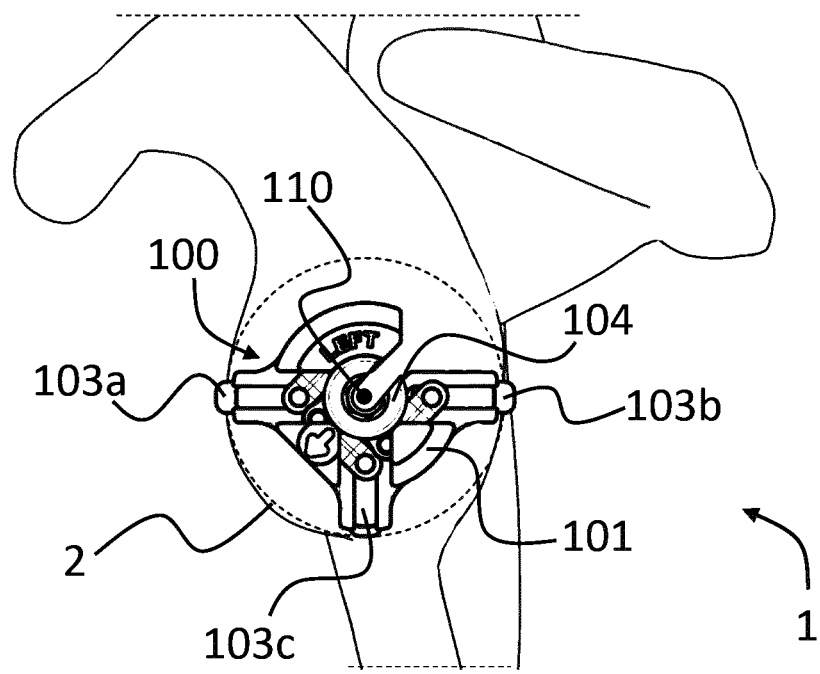
FIG. 8 shows a side schematic view of a scapula, in which a glenoid positioning device according to the present invention is positioned.

FIG. 8 shows a side schematic view of the scapula 1, in which the glenoid positioning device 100 is positioned in the use position.

According to what has already been described, in the glenoid positioning device 100 the three slide elements 103a, 103b and 103c are configured to identify a circular area 2 of the glenoid cavity, whereas the central spindle 104 and the related reference through-hole 110 are configured to identify a center 3 of the circular area 2, in particular for positioning a reference, for instance a Kirschner wire, in a center of the glenoid fossa of scapula.

For illustrative and non-limiting purposes, an example of use of the glenoid positioning device 100 according to the present invention is now provided.

First of all, the glenoid positioning device 100 is positioned onto the lower part of the glenoid cavity.

Afterwards, through the rotation of the central spindle 104, the slide elements 103a, 103b and 103c are radially extended until they pass the glenoid margin in the sagittal plane in the fore/aft direction.

Subsequently, still rotating the central spindle 104, the slide elements 103a, 103b and 103c are radially retracted until they obtain the contact between the internal part of the ends 109a and 109b of the elements 103a and 103b and the glenoid margin, in the maximum width area of the latter on the sagittal plane in the fore/aft direction.

The subsequent step provides to visually verify that the end of the slide element 103c is approximately located on the lowest point of the glenoid fossa of scapula; in this way the three points necessary to determine the circumference 2 that identifies the glenoid fossa of scapula have been identified.

Thus a reference, in the example a Kirschner wire 4, is inserted into the central spindle 104 using a reference through-hole 110 present therein and within the hub 101.

Advantageously, the point where the entry of the Kirschner wire 4 into the glenoid occurs, represents the center 3 of the glenoid fossa of scapula of the scapula 1, treated with the above glenoid positioning device 100.

Once the complete closure of the device has been obtained by means of the further rotation of the central spindle 104, the side access slots 111a and 111b both on the hub 101 and on the central spindle 104 are aligned to each other, and thus it is possible to remove the glenoid positioning device 100 from the reference, in this example from the Kirschner wire 4, provisionally implanted in the glenoid cavity, by passing the Kirschner wire 4 through the two aligned slots 111a and 111b.

Therefore, the radial stroke of the slide elements 103a, 103b and 103c is such as to pass, when they are radially extended, a glenoid margin in a sagittal plane in the fore/aft direction.

Figure 9:
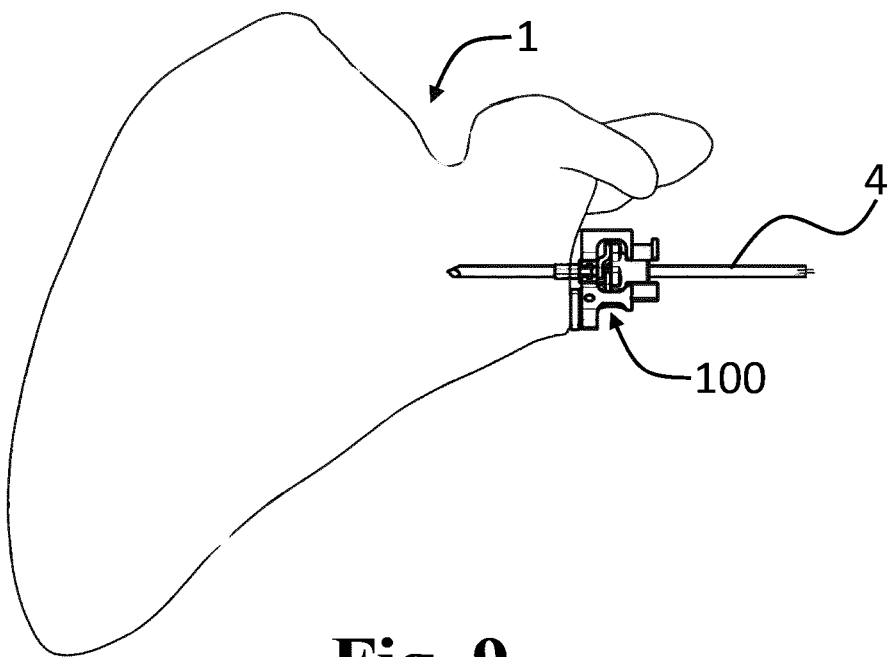
FIG. 9 shows a frontal schematic view of the scapula of FIG. 8, in which a Kirschner wire is associated with the glenoid positioning device.

FIG. 9 shows a frontal schematic view of the scapula of FIG. 8, in which a reference, for instance a Kirschner wire, is associated with the glenoid positioning device.

According to what has been already described, the glenoid positioning device 100 is configured to identify a center of the glenoid fossa of scapula for the accurate and repeatable positioning of a reference, such as for instance the Kirschner wire 4.

With the solution of the present invention it is provided that the glenoid positioning device 100 identifies the center 3 of the glenoid cavity with greater reliability, allowing a more accurate and repeatable positioning of a reference, constituted by a Kirschner wire 4, used during a shoulder prosthesis implantation.

The slide elements 103a, 103b and 103c allow identifying a circular area of a glenoid cavity, and the central spindle 104 is configured to identify a center 3 of the circular area 2 for the positioning of a reference in a center of a glenoid fossa of scapula.

Thus, advantageously, it is possible to position a reference in the center of the fossa of scapula of a glenoid cavity in an accurate and repeatable manner.

It is clear that, in order to meet contingent needs, further implementations and modifications of the present invention will be possible for the skilled in the art. The above described embodiment is thus to be intended as provided for illustrative and not limitative purposes.

What is claimed is:

1. A glenoid positioning device comprising:
    a hub with a reference through-hole and comprising three housings arranged radially;
    three slide elements slidably housed within said three housings respectively;
    a central spindle axially associated with said hub and rotatable therein;
    three connection bars connecting each of said three slide elements with said central spindle, respectively;
    wherein said three slide elements are configured to be radially extended and radially retracted synchronously with each other and in a controlled manner by the action of a control device associated with said hub, to interact with a glenoid cavity and identify a circular area of the glenoid cavity; and
    wherein said three slide elements are configured to be radially extended and radially retracted by the action of said three connection bars operated by a rotation of said central spindle.

2. The glenoid positioning device according to claim 1, wherein a first slide element and a second slide element of said three slide elements are opposite each other, and wherein said first slide element and said second slide element comprise respective protruding ends configured to externally grasp a glenoid portion of a scapula.

3. The glenoid positioning device according to claim 2, wherein a third slide element of said three slide elements is aligned transversally to said first slide element and to said second slide element, said third slide element being configured to provide a visual reference at its own end.

4. The glenoid positioning device according to claim 2, wherein said protruding ends comprise internal surfaces that are machined so as to increase friction with a bone surface.

5. The glenoid positioning device according to claim 1, wherein said hub and said central spindle comprise respective reference through-holes that are axially aligned and configured for the axial insertion of a reference.

6. The glenoid positioning device according to claim 5, wherein said hub and said central spindle comprise respective side access slots to said respective reference through-holes, said side access slots being aligned to each other for an angular position of said rotation of said central spindle to allow the removal of said glenoid positioning device from said reference positioned in the glenoid cavity.

7. The glenoid positioning device according to claim 1, wherein said slide elements are configured to be extended or retracted with respective ends lying on a same circumference, said circumference having a radius that is variable with said rotation of said central spindle.

8. The glenoid positioning device according to claim 1, wherein said three connection bars are connected to said central spindle and to said three slide elements, respectively, by means of pins, thus providing a triple rod-crank type system.

9. The glenoid positioning device according to claim 8, wherein said triple rod-crank type system is configured, during said rotation of said central spindle, to extend said three slide elements from a position of maximum closure to a position of maximum opening and, during said rotation of said central spindle in an opposite direction, to retract said three slide elements in a further position that is at least partially retracted.

10. The glenoid positioning device according to claim 1, wherein a stroke of said three slide elements, when radially extended, is such as to pass a glenoid margin in a sagittal plane in the fore/aft direction.

11. The glenoid positioning device according to claim 1, wherein said hub further comprises a pin configured to engage into a radial groove of said central spindle, to allow said rotation of said central spindle, thus preventing a translation of said central spindle in an axial direction.

12. The glenoid positioning device according to claim 1, wherein said central spindle is configured to identify a center of a circular area of a glenoid cavity for positioning a reference in a center of a glenoid fossa of scapula.

13. The glenoid positioning device according to claim 12, wherein said reference is a K-wire.

* * * * *